(12) United States Patent
Haynes et al.

(10) Patent No.: US 9,427,293 B2
(45) Date of Patent: Aug. 30, 2016

(54) ELECTRIC TOOTHBRUSH ATTACHMENT MECHANISM

(71) Applicant: Den-Mat Holdings, LLC, Lompoc, CA (US)

(72) Inventors: Ronald Wayne Haynes, Fairfield Bay, AR (US); Ian Thorne, Thornton, CO (US); Jered Harvey Dean, Arvada, CO (US); Emanuel Guzman, Aurora, CO (US); Sean Michael Cole, Denver, CO (US); John R. Gardner, Parker, CO (US); Scott Douglas Nelson, Denver, CO (US)

(73) Assignee: Den-Mat Holdings, LLC, Lampoc, CA (US)

( * ) Notice: Subject to any disclaimer, the term of this patent is extended or adjusted under 35 U.S.C. 154(b) by 62 days.

(21) Appl. No.: 14/068,733

(22) Filed: Oct. 31, 2013

(65) Prior Publication Data

US 2014/0115801 A1    May 1, 2014

Related U.S. Application Data

(60) Provisional application No. 61/720,931, filed on Oct. 31, 2012, provisional application No. 61/720,894, filed on Oct. 31, 2012.

(51) Int. Cl.
*A61C 17/22* (2006.01)
*A61C 17/26* (2006.01)

(52) U.S. Cl.
CPC ............ *A61C 17/26* (2013.01); *A61C 17/222* (2013.01); *Y10T 29/49826* (2015.01)

(58) Field of Classification Search
CPC .. A61C 17/22; A61C 17/222; A61C 17/225; A61C 17/24; A61C 17/26; A61C 17/32; A61C 17/34; A61C 17/3409; A61C 17/3427; A61C 17/3436
USPC ................... 15/22.1, 22.2, 23, 28; 132/322; 433/142, 125; 601/126
See application file for complete search history.

(56) References Cited

U.S. PATENT DOCUMENTS

| | | | |
|---|---|---|---|
| 3,088,148 A * | 5/1963 | Moret | 15/22.1 |
| 3,158,884 A | 12/1964 | Monti-Buzzetti | |
| 3,182,345 A * | 5/1965 | Smith | 15/176.6 |
| 3,278,963 A * | 10/1966 | Bond | 15/22.1 |

(Continued)

FOREIGN PATENT DOCUMENTS

| | | | |
|---|---|---|---|
| DE | 19508932 | * | 9/1996 |
| JP | 8-322641 | * | 12/1996 |
| WO | 87/00405 | * | 1/1987 |

*Primary Examiner* — Mark Spisich
(74) *Attorney, Agent, or Firm* — Frederick W. Tong

(57) ABSTRACT

A toothbrush that includes a brushing attachment and a handle is described. The brushing attachment includes a main body portion that includes a hollow neck and a head. The neck includes a skirt portion with an attachment opening and the head includes a cleaning member opening. The handle includes a main body portion that houses a motor, and a male attachment member extending upwardly from the main body portion that is at least partially received in the attachment opening in the brushing attachment. The male attachment member includes at least a first retention rib that is received in a first retention recess defined in the inner surface of the neck of the brushing attachment, and the inner surface of the neck includes a first retention lug extending outwardly therefrom that is positioned below the first retention rib.

17 Claims, 10 Drawing Sheets

(56) References Cited

U.S. PATENT DOCUMENTS

| | | | |
|---|---|---|---|
| 3,369,265 A * | 2/1968 | Halberstadt et al. | 15/22.1 |
| 3,927,435 A * | 12/1975 | Moret et al. | 15/176.1 |
| 4,123,845 A * | 11/1978 | Fattaleh | 433/99 |
| 4,697,949 A | 10/1987 | Perez | |
| 4,780,924 A * | 11/1988 | Hansen et al. | 15/176.1 |
| 4,827,550 A * | 5/1989 | Graham et al. | 15/22.1 |
| 5,020,994 A * | 6/1991 | Huang | 433/126 |
| 5,353,460 A * | 10/1994 | Bauman | 15/22.1 |
| 5,365,627 A * | 11/1994 | Jousson et al. | 15/22.1 |
| 2012/0021382 A1 * | 1/2012 | Dickie | 433/216 |

* cited by examiner

US 9,427,293 B2

ELECTRIC TOOTHBRUSH ATTACHMENT MECHANISM

RELATED APPLICATIONS

This application claims the benefit of U.S. Provisional Application No. 61/720,931,filed Oct. 31,2012 and U.S. Provisional Application No. 61/720,894,filed Oct. 31,2012, both of which are herein incorporated by reference in its entirety.

FIELD OF THE INVENTION

The present invention relates to an attachment mechanism, and more particularly to an attachment mechanism for an electric toothbrush.

BACKGROUND OF THE INVENTION

After a certain amount of use, the brush heads on electric toothbrushes often wear out and need to be replaced. An attachment mechanism or system for connecting a new brush head to the handle that is easy for a consumer to use is desirable.

SUMMARY OF THE PREFERRED EMBODIMENTS

The invention provides a snap-on design with a distinct and relatively easily controlled snap configuration. A molded ring on the male attachment member of the handle snaps into a molded undercut that is formed from the outside of the brushing attachment or through a collapsible core arrangement.

The invention allows the attachment of the brushing attachment to the handle by pushing the brush head onto the handle in a direction generally parallel to the axis of the drive mechanism (see arrow A1 in FIG. 13A). This eliminates the need for rotation to secure the brushing attachment to the handle and provides a more definite and predictable location of the snap features.

Generally, the invention includes a battery powered toothbrush handle male attachment member with a tapered surface to provide positive positioning during attachment of the brushing attachment and a positive stop surface. A retention ring or rib that is molded with side pulls or the like provides a controlled distance from the positive stop surface. An alignment channel or feature to provide orientation to the brushing attachment. A path for the motivating force member through the center of the device as driven by an appropriate mechanism, such as the drive mechanism disclosed in U.S. Provisional patent application Ser. No. 61/720,894, filed on Oct. 31, 2012 which is incorporated herein by reference for all purposes, in the power handle. The brushing attachment includes at least one retention lug with a lead-in ramp or radius to provide a path for retention rib during attachment to the handle and an alignment rib that mates with the alignment channel. A molded feature such as a collapsible core, external cavity or slide or other mechanism forms a distinct position and configuration of the retention rib. This may be a recess defined in the inner surface or a hole that extends through to the outside surface. The retention lug can also include a lead-out ramp or radius to provide a path for the retention rib during removal from the handle.

In use, a portion of the brushing attachment flexes outwardly as the retention lug rides up and over the retention rib when the brushing attachment is pressed onto the male attachment member.

In accordance with a first aspect of the present invention there is provided a toothbrush that includes a brushing attachment and a handle. The brushing attachment includes a main body portion that includes a hollow neck and a head. The neck includes a skirt portion with an attachment opening and the head includes a cleaning member opening. The handle includes a main body portion that houses a motor, and a male attachment member extending upwardly from the main body portion that is at least partially received in the attachment opening in the brushing attachment. The male attachment member includes at least a first retention rib that is received in a first retention recess defined in the inner surface of the neck of the brushing attachment, and the inner surface of the neck includes a first retention lug extending outwardly therefrom that is positioned below the first retention rib.

In a preferred embodiment, the male attachment member includes a second retention rib opposed to the first retention rib that is received in a second retention recess defined in the inner surface of the neck of the brushing attachment, and the inner surface of the neck includes a second retention lug extending outwardly therefrom that is positioned below the second retention rib. Preferably, the male attachment member includes a tapered outer surface that is generally cylindrical in shape and the first and second attachment ribs extend at least partially circumferentially about the male attachment member. In a preferred embodiment, the inner surface of the neck includes at least a first stop member positioned above the first retention recess and a second stop member positioned above the second retention recess. Preferably, the first retention lug includes an inclined bottom surface and an inclined top surface. The inner surface of the neck includes a longitudinally extending alignment rib that is received in a longitudinally extending alignment groove in the male attachment member.

In accordance with another aspect of the present invention there is provided a method that includes providing an electric toothbrush handle that includes a main body portion that houses a motor, and a male attachment member extending upwardly from the main body portion, providing a brushing attachment that includes a main body portion that includes a hollow head and neck having a skirt with an attachment opening, inserting the male attachment member into the attachment opening, engaging a retention lug on an inner surface of the neck of the brushing attachment with a retention rib on the male attachment member, thereby causing the skirt to flex outwardly, and seating the retention rib in a retention recess defined in the inner surface of the neck and positioned above the retention lug.

In a preferred embodiment, the retention lug includes an inclined surface, and the engagement of the retention rib with the inclined surface causes the skirt to flex outwardly. Preferably, the male attachment member includes a tapered outer surface that is generally cylindrical in shape and the inner surface of the neck includes a includes at least a first stop member positioned above the retention recess. In a preferred embodiment, the inner surface of the neck includes a longitudinally extending alignment rib, and the method further comprises the step of inserting the alignment rib into a longitudinally extending alignment groove in the male attachment member.

In accordance with another aspect of the present invention there is provided a brushing attachment for use with a toothbrush. The brushing attachment includes a main body portion that includes a hollow neck and a head. The neck includes a skirt portion with an attachment opening and the head includes a cleaning member opening. The brushing attachment also includes a first retention recess defined in an inner surface of the neck, and a first retention lug disposed on the inner surface of the neck and positioned below the first retention recess.

In a preferred embodiment, the brushing attachment includes a second retention recess defined in an inner surface of the neck and a second retention lug with an inclined bottom surface disposed on the inner surface of the neck and positioned below the second retention recess. The inner surface of the neck preferably includes at least a first stop member positioned above the first retention recess and a second stop member positioned above the second retention recess and the inner surface of the neck includes a longitudinally extending alignment rib.

The invention, together with additional features and advantages thereof, may be best understood by reference to the following description.

DETAILED DESCRIPTION OF THE PREFERRED EMBODIMENTS

Figure 1:
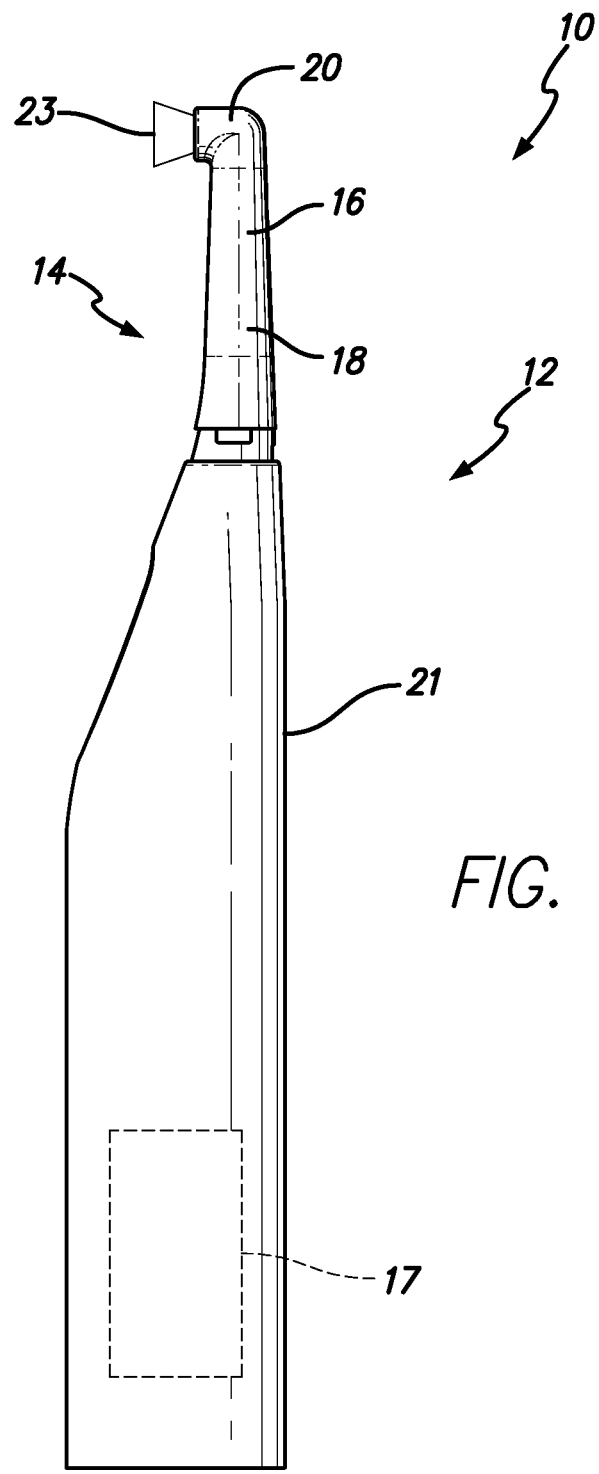
FIG. 1 is a side elevational view of a toothbrush that includes the attachment mechanism of the present invention.

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily are references to the same embodiment; and, such references mean at least one of the embodiments.

Reference in this specification to "one embodiment" or "an embodiment" means that a particular feature, structure, or characteristic described in connection with the embodiment is included in at least one embodiment of the-disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks: The use of highlighting has no influence on the scope and meaning of a term; the scope and meaning of a term is the same, in the same context, whether or not it is highlighted. It will be appreciated that the same thing can be said in more than one way.

Consequently, alternative language and synonyms may be used for any one or more of the terms discussed herein. Nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "upper," "lower," "side," "short," "long," "up," "down," and "below" used herein are merely for ease of description and refer to the orientation of the components as shown in the figures. It should be understood that any orientation of the components described herein is within the scope of the present invention.

Referring now to the drawings, which are for purposes of illustrating the present invention and not for purposes of limiting the same, FIGS. 1-13 show an electric toothbrush 10 having a handle 12 and a brushing attachment 14. It will be understood that the electrical components of the handle 12, (e.g., the motor 17, battery, etc.) and the components for transmitting motion (e.g., rotational motion) through the interior of the handle and brushing attachment and to the bristles are known. Therefore, a discussion of these components will be omitted. Generally, the powered toothbrush includes the handle 12 with a male attachment member 19 that receives the brushing attachment 14.

As shown in FIGS. 2-8, generally, the brushing attachment 14 includes a main body portion 16 that includes a hollow neck 18 and a head 20. The neck 18 includes a skirt portion 34 with an attachment opening 24 and the head 20 includes a cleaning member opening 25 through which extends a cleaning member 23 (e.g., bristles). It will be appreciated by those skilled in the art, that brushing attachment 14 can include brushing surfaces other than the bristles, such as massagers, flossers or other tooth cleaning technology known in the art (these are all referred to herein generally as "cleaning members"). Internally, the brushing attachment 14 includes gearing or other energy translation mechanism for translating the rotational energy through the ninety degree bend from an internal drive shaft or the like to the cleaning member 23.

Figure 10:
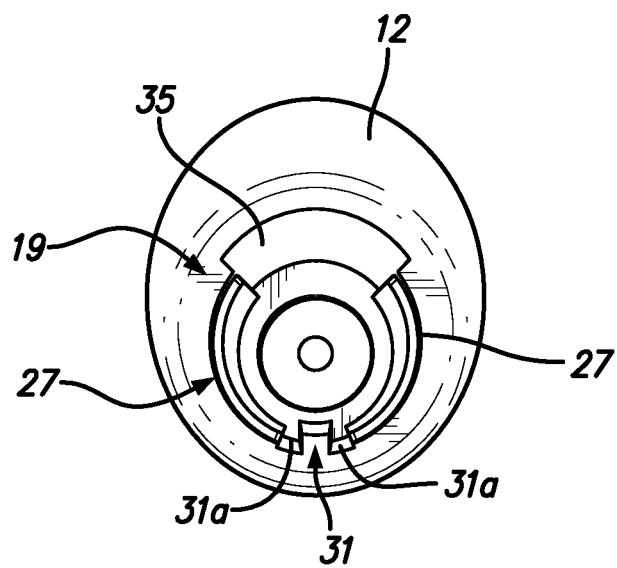
FIG. 10 is a top plan view of the male attachment member of the handle.
Figure 11:
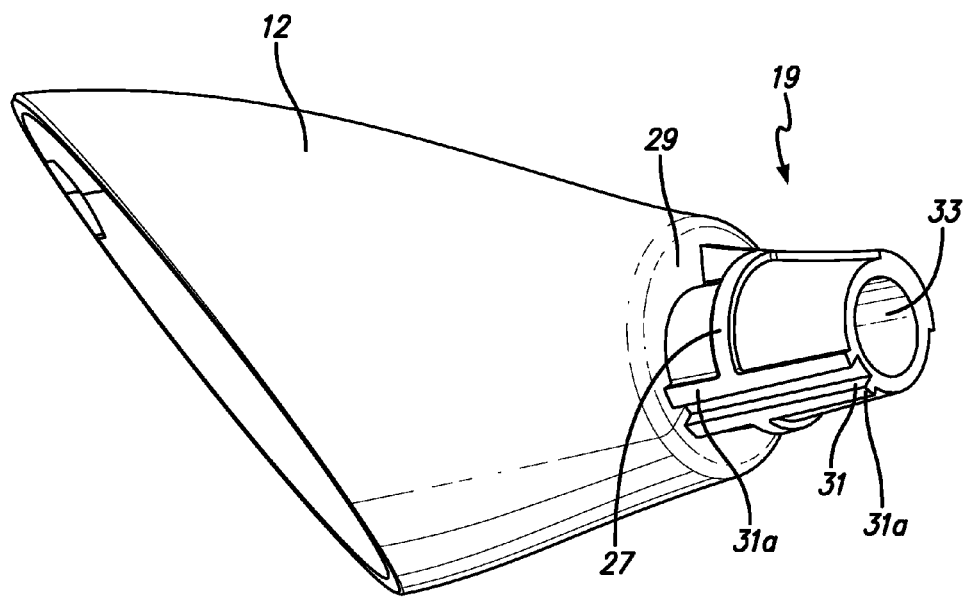
FIG. 11 is a perspective view of a portion of the handle including the male attachment member.
Figure 12:
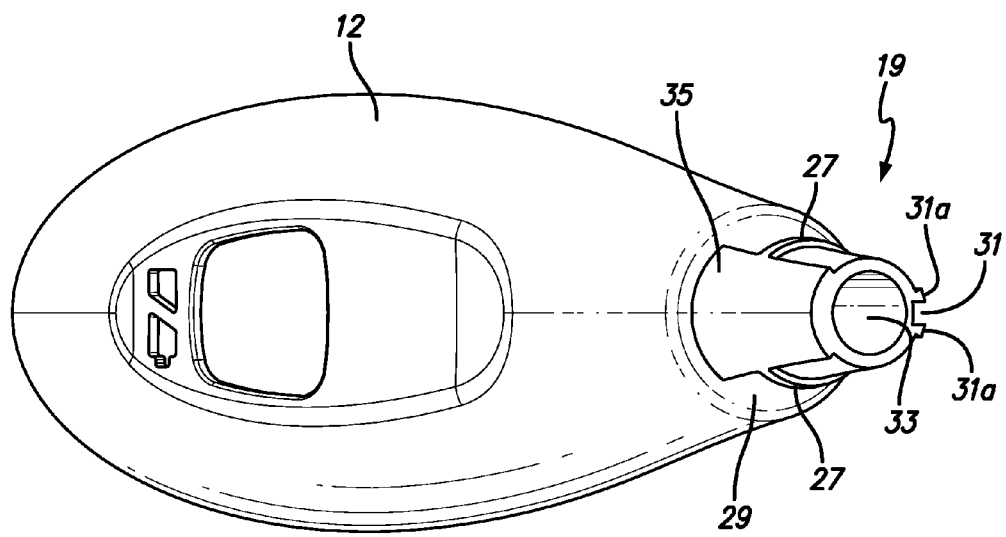
FIG. 12 is another perspective view of a portion of the handle including the male attachment member.
Figure 13A:
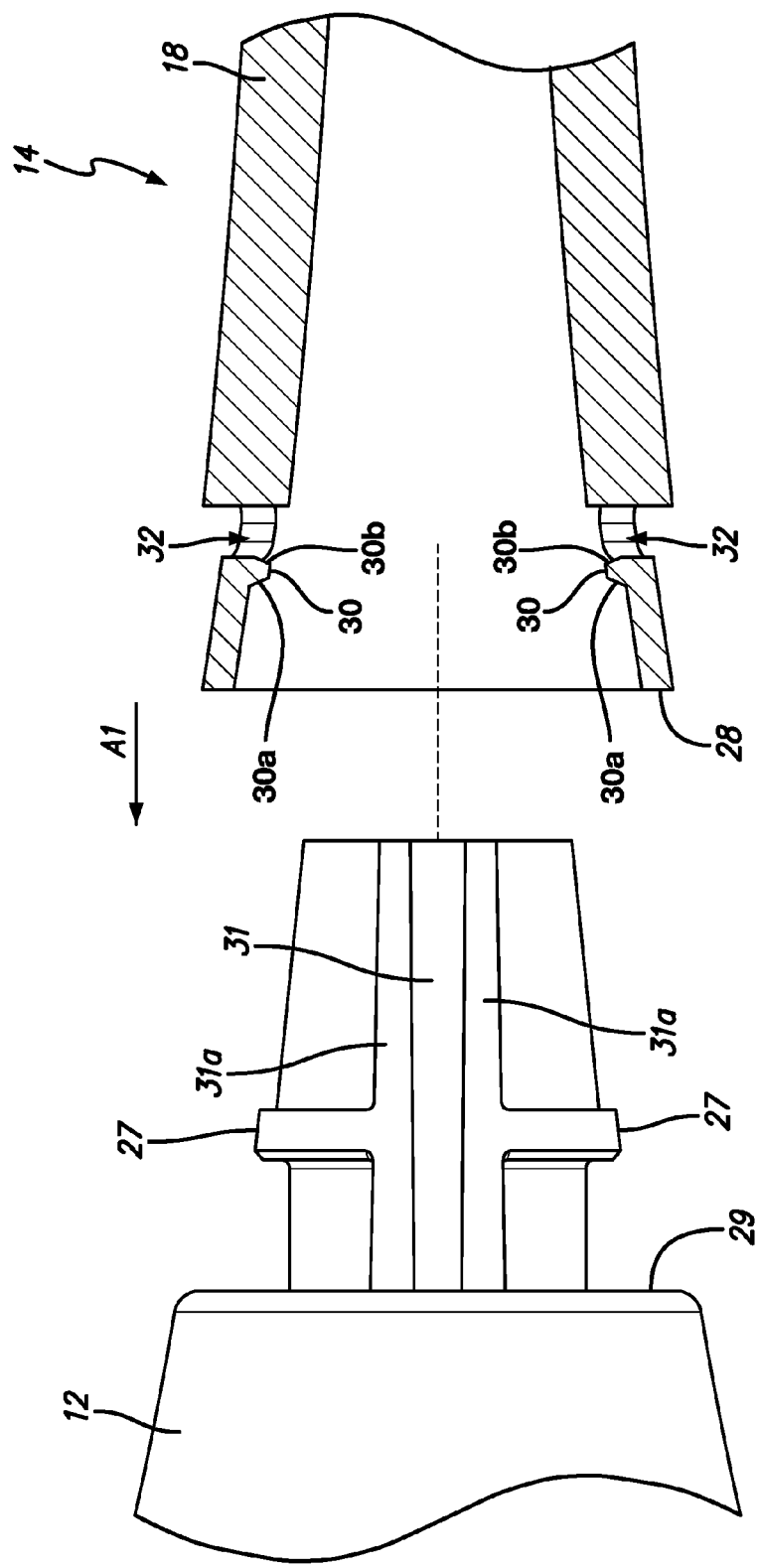
FIG. 13A is a cross-sectional view of a portion of the brushing attachment prior to being attached to the male attachment member of the handle.
Figure 13B:
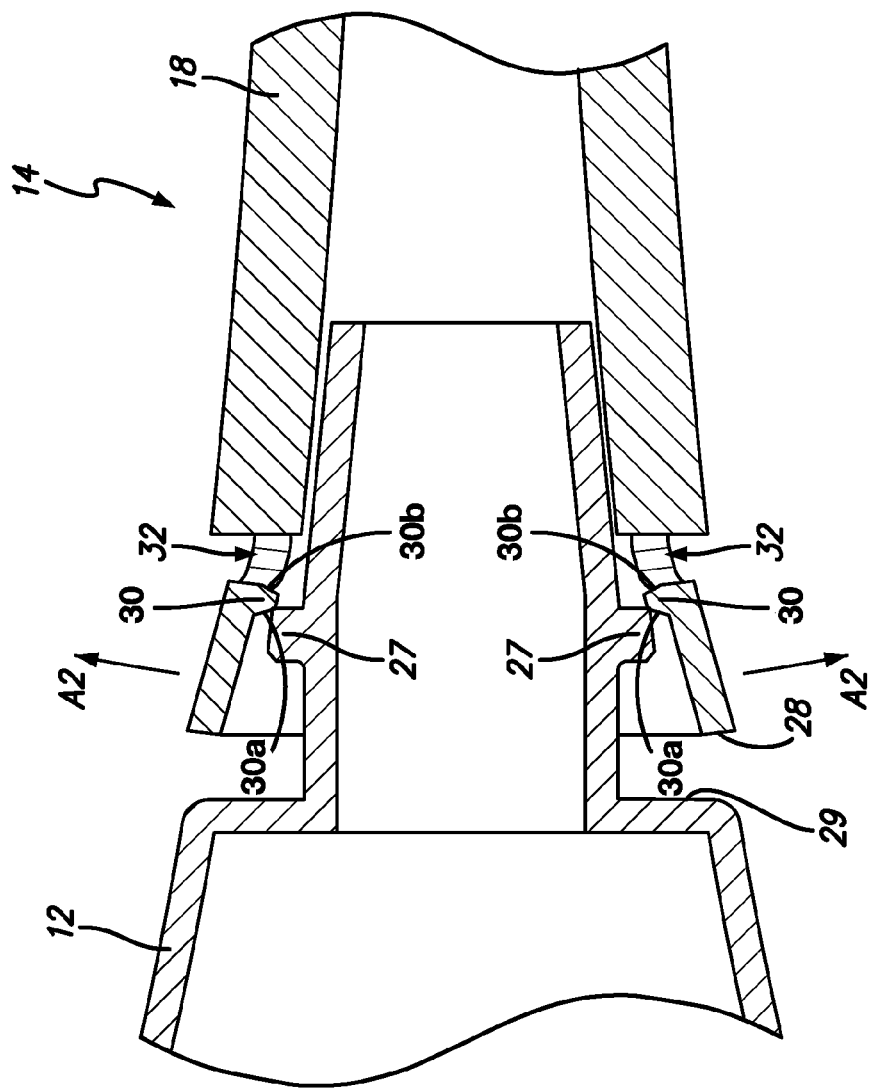
FIG. 13B is a cross-sectional view of a portion of the brushing attachment while being attached to the male attachment member of the handle.
Figure 13C:
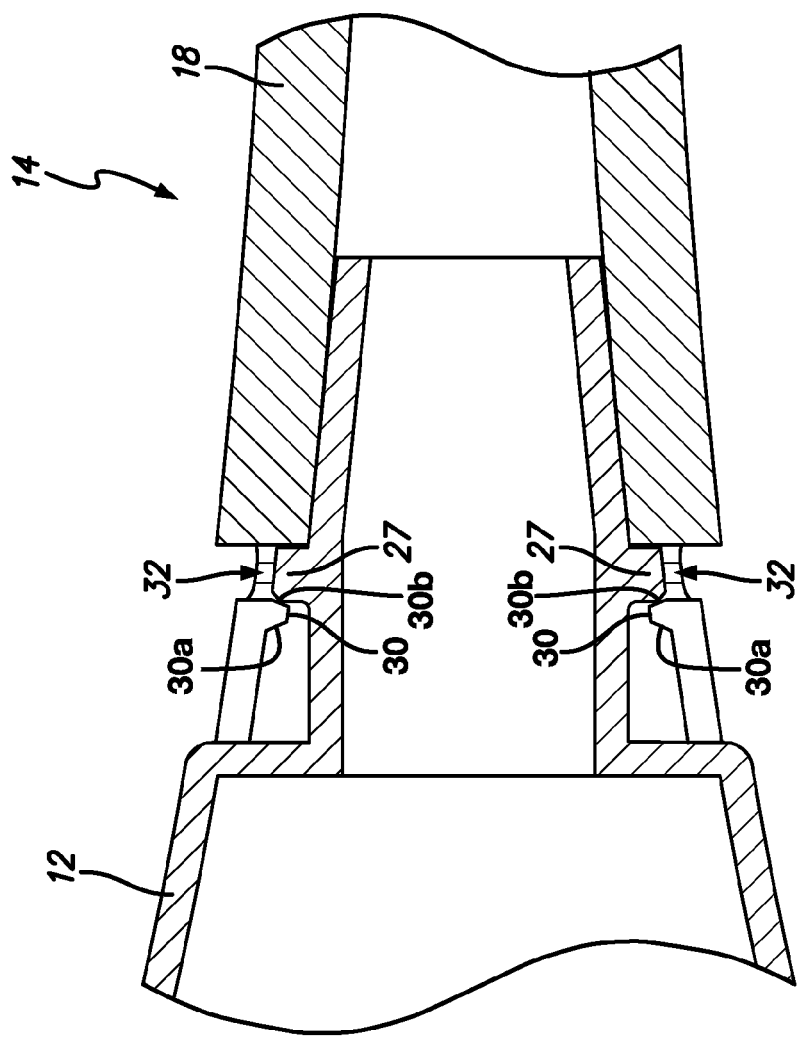
FIG. 13C is a cross-sectional view of a portion of the brushing attachment after being attached to the male attachment member of the handle.

As shown in FIGS. 9-13C, the handle 12 generally includes a main body portion 21 that houses the motor 17, and the male attachment member 19 extending upwardly from the main body portion 21. As shown in FIG. 13C, in use, the male attachment member 19 is at least partially received in the attachment opening 24 defined in the brushing attachment 14 and extends up into the hollow neck 18. In a preferred embodiment, the male attachment member 19 includes at least one retention rib 27 extending in a circumferential direction. In a preferred embodiment, as shown in FIG. 10, the handle 12 includes two retention ribs 27 disposed on opposite sides of the male attachment member 19. As explained more fully below, the retention ribs 27 are received in retention recesses 32 that are defined in or on the inner surface 18a of the neck 18 of the brushing attachment 14 to provide retention of the brushing mechanism.

In a preferred embodiment, the male attachment member 19 includes a stop surface 29 to help control the final installed position of the brushing attachment 14. The brushing attachment 14 includes a lower stop surface 28 that interfaces with the stop surface 29 of the handle 12. The male attachment member 19 also preferably includes an alignment groove 31 that is defined by two longitudinally extending protrusions 31a and that receives an alignment rib 22 on the brushing attachment 14 to orient the brushing attachment 14 during attachment to the handle 12. In another embodiment the alignment rib 22 and groove 31 can be omitted.

The male attachment member 19 also includes a central path 33 for a drive motivation mechanism and energy transfer between the handle 12 and the brushing attachment 14.

As shown in FIGS. 11-12, the male attachment member 19 preferably includes a tapered interface or outer surface 35 that interacts with a tapered inner surface 26 on the brushing attachment 14 to help align the brushing attachment 14 when the male attachment member 19 and brushing attachment 14 are attached to one another.

Figure 2:
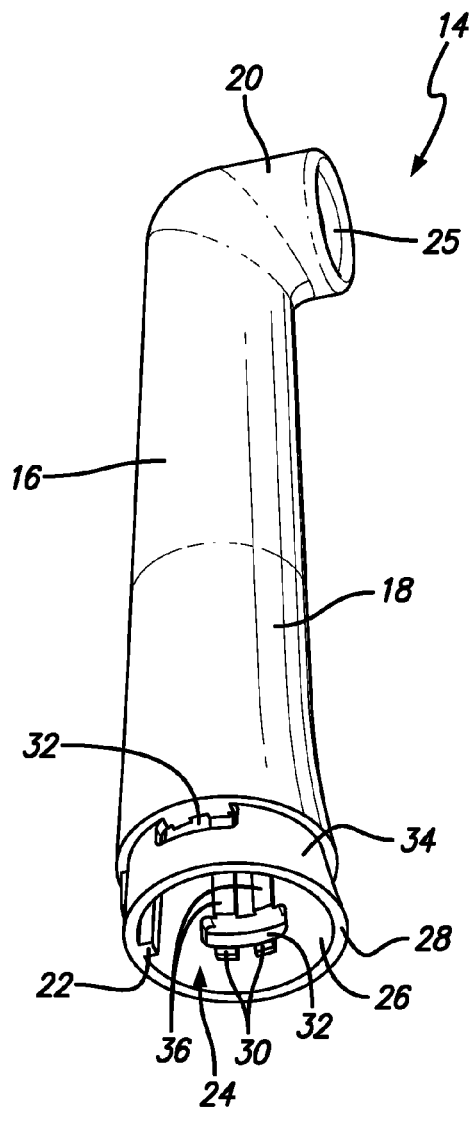
FIG. 2 is a perspective view of the brushing attachment.
Figure 3:
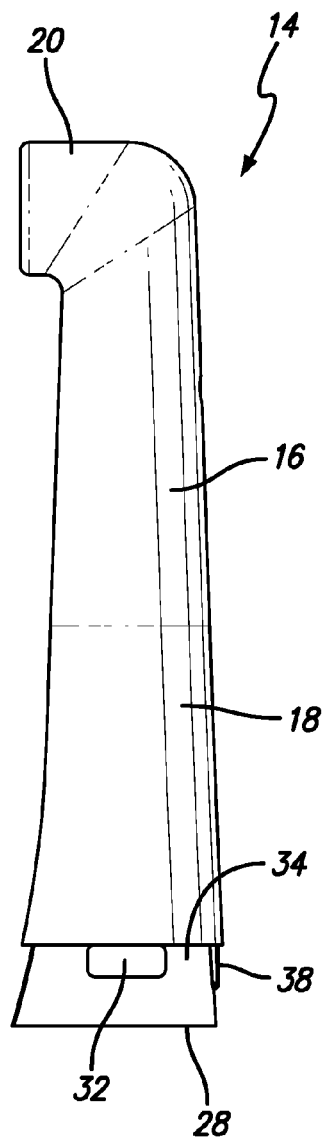
FIG. 3 is a side elevational view of the brushing attachment.
Figures 4, 5:
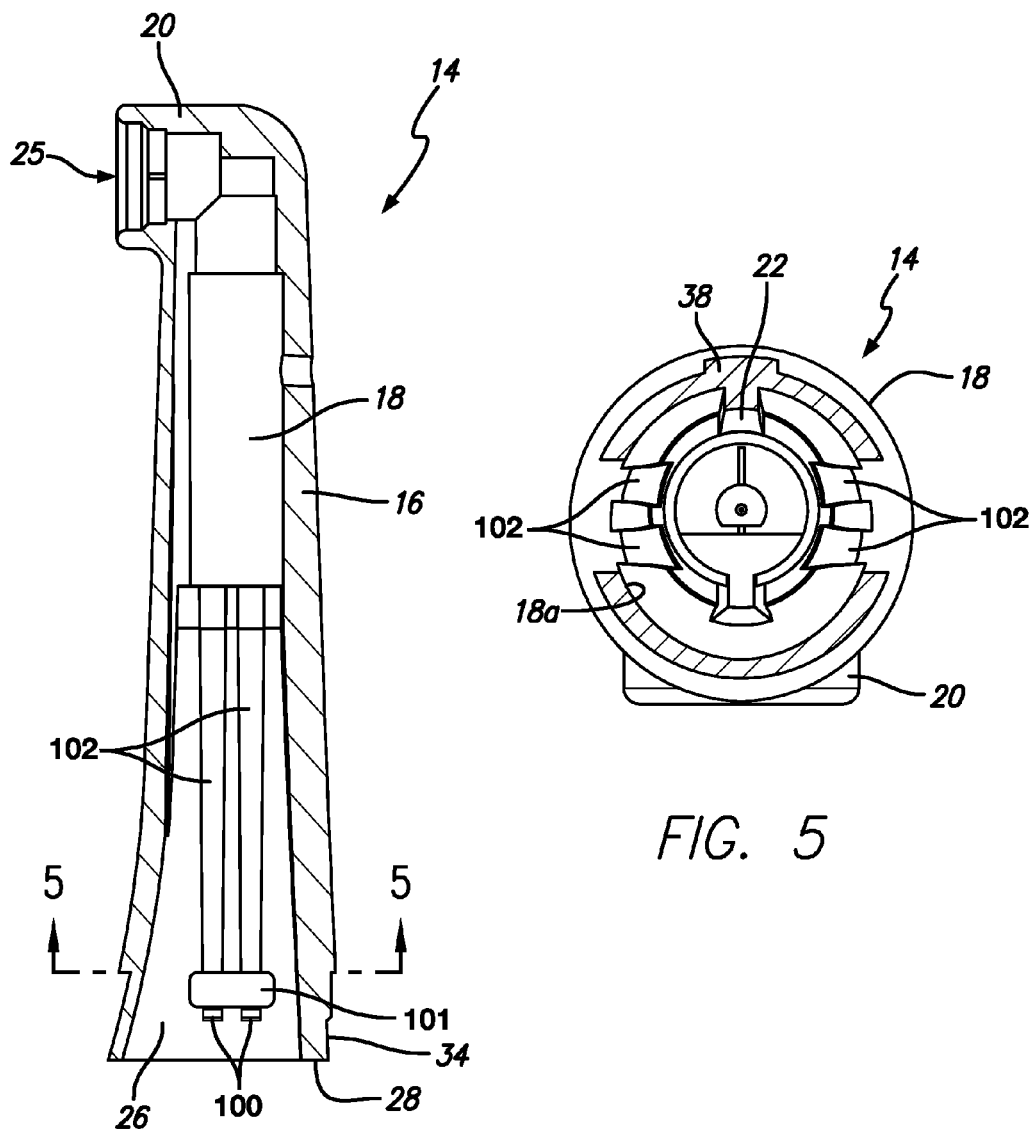
FIG. 4 is a cross-sectional side elevational view of the brushing attachment.
FIG. 5 is a cross-sectional end view taken along line 5-5 of FIG. 4.
Figure 6:
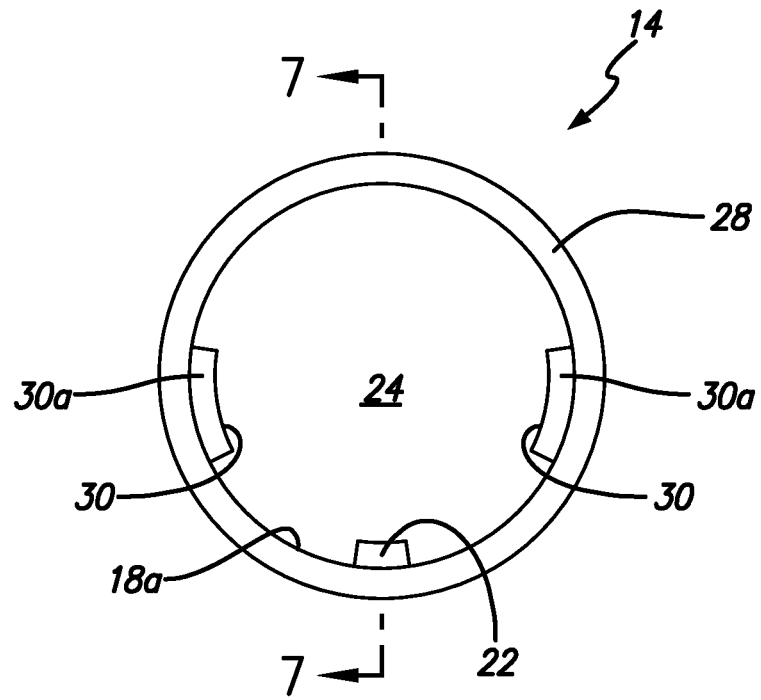
FIG. 6 is a bottom plan view of the brushing attachment.
Figure 7:
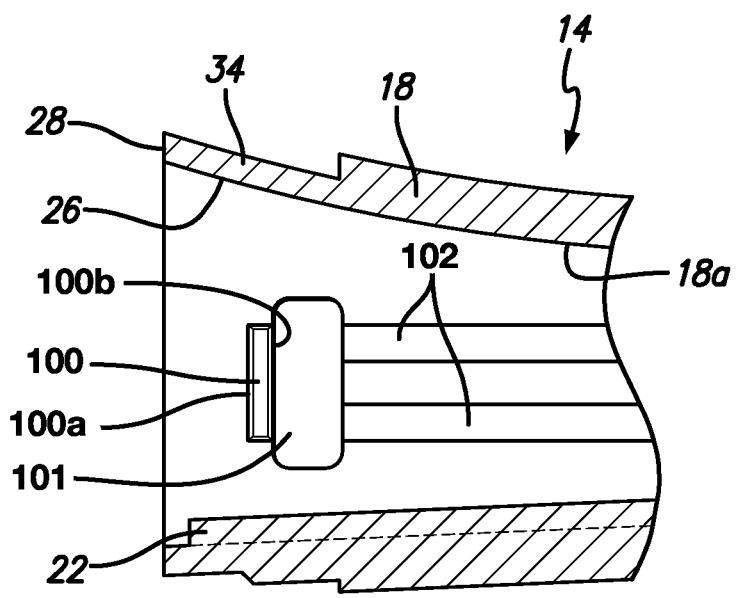
FIG. 7 is a cross-sectional view of a portion of the brushing attachment taken along line 7-7 of FIG. 6.
Figure 8:
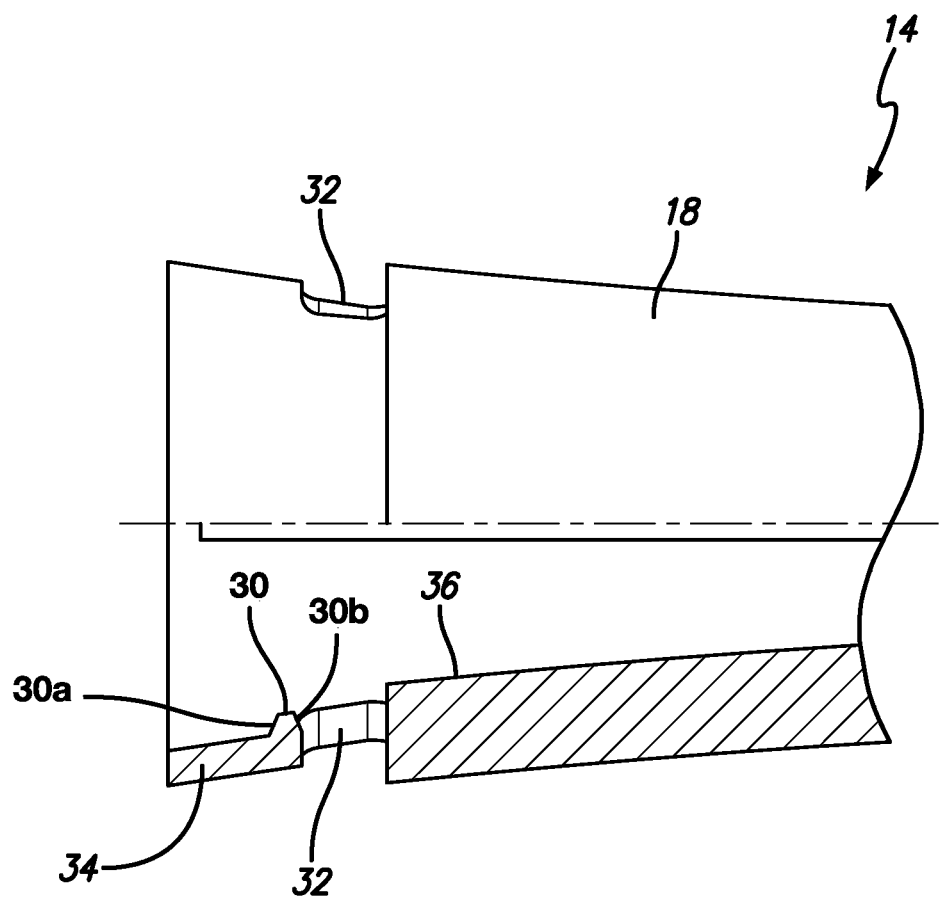
FIG. 8 is a partial cross-sectional view of a portion of the brushing attachment.
Figure 9:
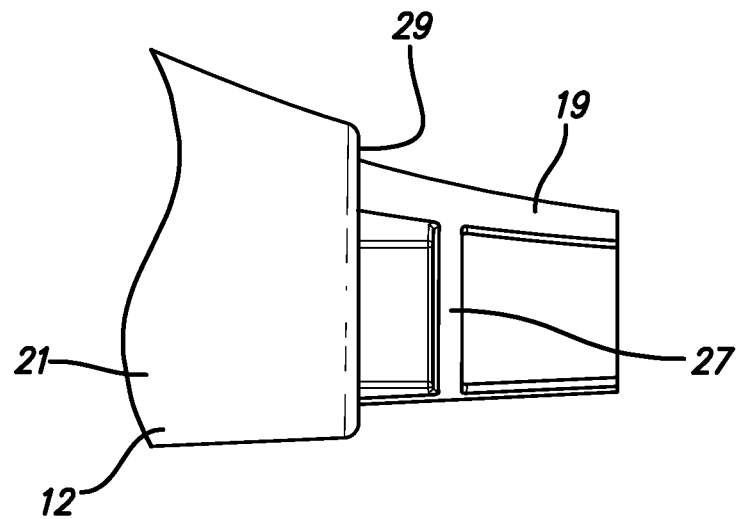
FIG. 9 is a side elevational view of the male attachment member of the handle.

As shown in FIGS. 2-4, the brushing attachment 14 includes retention lugs 30 and recesses 32. Recesses 32 can be defined in the inner surface 18a of the neck or can extend all the way through, as shown in FIG. 3. Preferably, the lugs 30 include lead in ramps, inclined surfaces 30a (or curved surfaces) that engage the retention ribs 27 during attachment. As shown in FIGS. 13A-13C, the skirt portion 34 of the brushing attachment flexes outwardly (see arrows A2) when the lugs 30 ride up and over the retention ribs 27 (as a result of ramps 30a) and the retention ribs 27 are then seated in recesses 32. In the alternative, the ramps can be disposed on the retention ribs 27.

As discussed, preferably, the skirt portion 34 of the brushing attachment 14 flexes as the interfering retention rib 27 and lug 30 are engaged. In a preferred embodiment, the brushing attachment 14 can include stop members 36 that engage the retention ribs 27 and prevent any further upward movement thereof The brushing attachment 14 can also include ramps 30b to facilitate removal of the brushing attachment 14 from the handle 12.

The brushing attachment 14 can also include a ring (not shown) that covers the skirt portion 34. The ring can be aligned or positioned with a positioning protrusion 38 on the skirt portion 34.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof Additionally, the words "herein," "above," "below," and words of similar import, when used in this application, shall refer to this application as a whole and not to any particular portions of this application. Where the context permits, words in the above Detailed Description of the Preferred Embodiments using the singular or plural number may also include the plural or singular number respectively. The word "or" in reference to a list of two or more items, covers all of the following interpretations of the word: any of the items in the list, all of the items in the list, and any combination of the items in the list.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. Further any specific numbers noted herein are only examples: alternative implementations may employ differing values or ranges.

Any patents and applications and other references noted above, including any that may be listed in accompanying filing papers, are incorporated herein by reference in their entirety. Aspects of the disclosure can be modified, if necessary, to employ the systems, functions, and concepts of the various references described above to provide yet further embodiments of the disclosure.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A toothbrush comprising:
   a brushing attachment that includes a main body portion that includes a hollow neck and a head, wherein the neck includes a skirt portion with a generally circular shaped attachment opening and the head includes a cleaning member opening,
   a handle that includes a main body portion that houses a motor, and a generally cylindrically shaped male attachment member extending upwardly from the main body portion that is at least partially received in the attachment opening in the brushing attachment, wherein the male attachment member includes at least a first retention rib which extends circumferentially around said male attachment member that is received in a first retention recess defined in the inner surface of the neck of the brushing attachment, and wherein the inner surface of the neck includes a first retention lug extending outwardly therefrom that is positioned below the first retention rib.

2. The toothbrush of claim 1 wherein the male attachment member includes a second retention rib which extends circumferentially around said male attachment member and is opposed to the first retention rib that is received in a second retention recess defined in the inner surface of the neck of the brushing attachment, and wherein the inner surface of the neck includes a second retention lug extending outwardly therefrom that is positioned below the second retention rib.

3. The toothbrush of claim 2 wherein the male attachment member includes a tapered outer surface.

4. The toothbrush of claim 3 wherein the inner surface of the neck includes at least a first stop member positioned above the first retention recess and a second stop member positioned above the second retention recess.

5. The toothbrush of claim 1 wherein the first retention lug includes an inclined bottom surface.

6. The toothbrush of claim 5 wherein the first retention lug includes an inclined top surface.

7. The toothbrush of claim 1 wherein the inner surface of the neck includes a longitudinally extending alignment rib that is received in a longitudinally extending alignment groove in the male attachment member.

8. A method comprising the steps of:
providing an electric toothbrush handle that includes a main body portion that houses a motor, and a generally cylindrically shaped male attachment member extending upwardly from the main body portion,
providing a brushing attachment that includes a main body portion that includes a hollow head and neck having a skirt with an generally circular shaped attachment opening,
inserting the male attachment member into the attachment opening,
engaging a retention lug on an inner surface of the neck of the brushing attachment with a retention rib on the male attachment member, thereby causing the skirt to flex outwardly, and
seating the retention rib in a retention recess defined in the inner surface of the neck and positioned above the retention lug.

9. The method of claim 8 wherein the retention lug includes an inclined surface, and wherein the engagement of the retention rib with the inclined surface causes the skirt to flex outwardly.

10. The method of claim 9 wherein the male attachment member includes a tapered outer surface.

11. The method of claim 10 wherein the inner surface of the neck includes at least a first stop member positioned above the retention recess.

12. The method of claim 8 wherein the inner surface of the neck includes a longitudinally extending alignment rib, and wherein the method further comprises the step of inserting the alignment rib into a longitudinally extending alignment groove in the male attachment member.

13. A brushing attachment for use with a toothbrush, the brushing attachment comprising:
a main body portion that includes a hollow neck and a head, wherein the neck includes a skirt portion with a generally circular shaped attachment opening and the head includes a cleaning member opening,
a longitudinally extending alignment rib located on an inner surface of said neck,
a first retention recess defined in said inner surface of the neck, and
a first retention lug disposed on the inner surface of the neck and positioned below the first retention recess.

14. The brushing attachment of claim 13 wherein the first retention lug includes an inclined bottom surface.

15. The brushing attachment of claim 14 further comprising a second retention recess defined in the inner surface of the neck, and a second retention lug with an inclined bottom surface disposed on the inner surface of the neck and positioned below the second retention recess.

16. The brushing attachment of claim 15 wherein the inner surface of the neck includes at least a first stop member positioned above the first retention recess and a second stop member positioned above the second retention recess.

17. The brushing attachment of claim 16 wherein the first and second retention lugs each include an inclined top surface.

* * * * *